(12) United States Patent
Visscher et al.

(10) Patent No.: US 7,510,520 B2
(45) Date of Patent: Mar. 31, 2009

(54) DEVICE FOR SENSING DISTAL END OF SOURCE WIRE IN AN AFTERLOADER

(75) Inventors: Arie Luite Visscher, Driebergen (NL); Johann Henning, Veenendaal (NL)

(73) Assignee: Nucletron B.V., Veenendaal (NL)

( * ) Notice: Subject to any disclaimer, the term of this patent is extended or adjusted under 35 U.S.C. 154(b) by 660 days.

(21) Appl. No.: 10/769,790

(22) Filed: Feb. 3, 2004

(65) Prior Publication Data
US 2004/0158115 A1    Aug. 12, 2004

(30) Foreign Application Priority Data
Feb. 5, 2003    (EP)    ................... 03075341

(51) Int. Cl.
*A61N 5/00* (2006.01)
(52) U.S. Cl. ........................................ 600/3
(58) Field of Classification Search .................. 600/3, 600/7; 601/3; 378/121
See application file for complete search history.

(56) References Cited
U.S. PATENT DOCUMENTS
5,851,172 A    12/1998 Bueche et al.
5,957,829 A    9/1999 Thornton
5,997,462 A *  12/1999 Loffler .................... 600/3
6,048,300 A    4/2000 Thornton et al.

FOREIGN PATENT DOCUMENTS
EP    0 791 374 A2    8/1997

* cited by examiner

*Primary Examiner*—John P Lacyk
(74) *Attorney, Agent, or Firm*—Birch, Stewart, Kolasch & Birch, LLP

(57) ABSTRACT

A device senses the presence of the distal end of a source wire in a reference position within a guidance channel of an afterloading apparatus for positioning an energy emitting source at a desired position within an animal body for radiation therapy treatment. The source wire is driven from the reference position through a guidance channel and a catheter tube. A sensing device detects the presence of the distal end of the wire. The sensing device has a pivotal lever element mounted near the guidance channel. The lever element is in a first position, when the distal end of the source wire is not present in its reference position and the lever element is in a second position, when the distal end is present in its reference position. The presence of the distal end and the energy emitting source can be sensed at several important operational positions.

21 Claims, 5 Drawing Sheets

DEVICE FOR SENSING DISTAL END OF SOURCE WIRE IN AN AFTERLOADER

This Nonprovisional application claims priority under 35 U.S.C. § 119(a) on Patent Application No. 03075341.2 filed in EUROPE on Feb. 5, 2003, the entire contents of which are hereby incorporated by reference.

FIELD OF THE INVENTION

The invention relates to a device for sensing the presence of the distal end of a source wire in a reference position within a guidance channel of an afterloading apparatus. The afterloading apparatus being used for positioning an energy emitting source fixed to said distal end of said source wire at a desired position within an animal body for radiation therapy treatment purposes. The source wire is driven from said reference position towards said desired position through said guidance channel and a catheter tube. The catheter tube is connected with one tube end to the afterloading apparatus and implanted with its other tube end in said animal body.

DESCRIPTION OF THE BACKGROUND ART

An afterloading apparatus is used for inserting an energy emitting source, for example a radioactive source from a reference position through a catheter tube into a desired location within an animal body for the purpose of radioactive treatment of for example cancer. The radioactive source at the end of the source wire must be handled with extreme care. Even short exposures at close distances can result in radiation injury. It is therefore extremely important that the afterloading apparatus, which controls the advancement and retraction of the source wire within the catheter tube, operates with a high reliability, and that it is configured to position the source wire within the catheter tube and the animal body in a controllable manner and with extreme accuracy and precision.

In the past, the control means of the afterloading apparatus which position the distal end of the source wire within the catheter tube have included special optical or mechanical sensors for sensing, when that distal end is located at a home or reference position within the afterloading apparatus.

Although such optical and mechanical sensors have operated generally satisfactorily in detecting the presence of the source wire's distal end at its reference position within the afterloading apparatus, the sensors' performance can degrade over time. This degradation is due, in part, to debris accumulating at the site of the sensor and to radiation damage in case of an opto sensor. One source of such debris is the catheter tube itself. As the source wire is cycled into and out of the catheter tube, a certain amount of catheter material is scraped away, and this material is drawn into the afterloader's drive mechanism. This debris can obscure the view of an optical sensor. An another disadvantage of the prior art systems is that small cable diameters of the drive wire can not obscure completely the light emitted by an opto sensor and therefore the tip of this cables can not be referenced exactly.

BRIEF SUMMARY OF THE INVENTION

The invention aims to overcome these drawbacks and to provide an afterloading apparatus provided with a sensing device according to the above preamble, which is capable of sensing the presence of the distal end and the energy emitting source at several important operational positions within the afterloading apparatus or patient, thus allowing a more exact positioning of the energy emitting source into the patient's body.

According to the invention the sensing device is characterized in that a lever element is pivotally mounted near said guidance channel, which lever element is in a first position, when said distal end of said source wire is not present in its reference position and whereas said lever element is in a second position, when said distal end is present in its reference position.

The use of a mechanical construction like a lever element obviates the drawbacks of the prior art, as the position of the lever element within the afterloading apparatus clearly and unambiguously will determine whether the distal end of the source wire (and hence the energy emitting source) is positioned exactly in its reference position or in a treatment position.

Thus, with this embodiment a highly reliable detection of the exact location of the energy emitting source within the afterloading apparatus is obtained.

Moreover with a further aspect the invention is characterized in that when said lever element is in a third position, said distal end is past said reference position, thus unambiguously indicating that the energy emitting source is outside its safe storage position.

More in particularly said lever element extends in said guidance channel when it is in its first position, unambiguously indicating the presence of the distal end of the source wire in at its storage position.

A more advantageous embodiment of the device according to the invention is characterized in that said lever element is biassed against a counterforce, said counterforce urging said lever element in its first position. More in particularly said device further comprises a spring for exerting said counterforce on said lever element.

The spring will improve the reliability, however the presence of a spring is not a necessity. The device may also operate without a spring, but operate based only on the weight of the lever. In that embodiment the gravitational force acts as a counter force.

For a proper control of the afterloading apparatus and more in particularly for a proper control of the advancement and retraction of the source wire and the energy emitting source detection means are present for detecting the presence of said lever element in said first, second or third position.

In the first embodiment said detection means comprise at least one light emitting element and one light detector mounted at both sides of said lever element, wherein said lever element is made of a light non-transparent material, and is provided with at least one through bore or with at least one notch. This embodiment uses the principle of interrupting a light path for obtaining a direct indication whether the distal end of the source wire is in its reference position or has passed that position. This measuring or detecting principle is more accurate than the detecting principle according to the prior art as mentioned above.

As according to the invention the optical path formed by said light emitting element and said light detector is located some distance away from the guidance channel, the effectiveness and accuracy of this detection principle will not be effected by any debris accumulated within the guidance channel. Also the light detector will not be irradiated by the energy emitting source travelling within the guidance channel, expanding its life span. Furthermore as the detection means do not interact with the energy emitting source and the source wire for obtaining information about the exact position of said source, source wire cables with a smaller diameter can be used.

Thus smaller catheter tubes can be inserted into the patient's body providing lesser discomfort and trauma.

In another embodiment the detection means are based on an electromagnetic principle as said lever element is at least partly made of a magnetic material and wherein said detection means comprises a Hall sensor.

Also other measuring principles based on magnetic induction, capacitive measurement, Hall effect detection or the use of a micro switch are possible.

Preferably two sensors of the same or different type are used in order to overcome a malfunction of the device in case one sensor fails. This increases the safety of the device according to the invention.

Preferably said energy emitting source can be chosen from a wide range of source types, like a radiowave antenna, a miniature X-ray source, a radioactive source, etc. Furthermore the source wire can be constructed as a optical wire, a coaxial cable or a combination of a coax cable and an optical wire. Also the source wire can be constructed as a nickle-titanium alloy wire or a combination of an optical wire surrounded by a nickle-titanium alloy tube.

The invention also relates to an afterloading apparatus provided with a sensing device according to the invention.

BRIEF DESCRIPTION OF THE DRAWINGS

The invention will now be described with reference to the accompanying drawings, which drawings show.

DETAILED DESCRIPTION OF THE INVENTION

Figure 1:
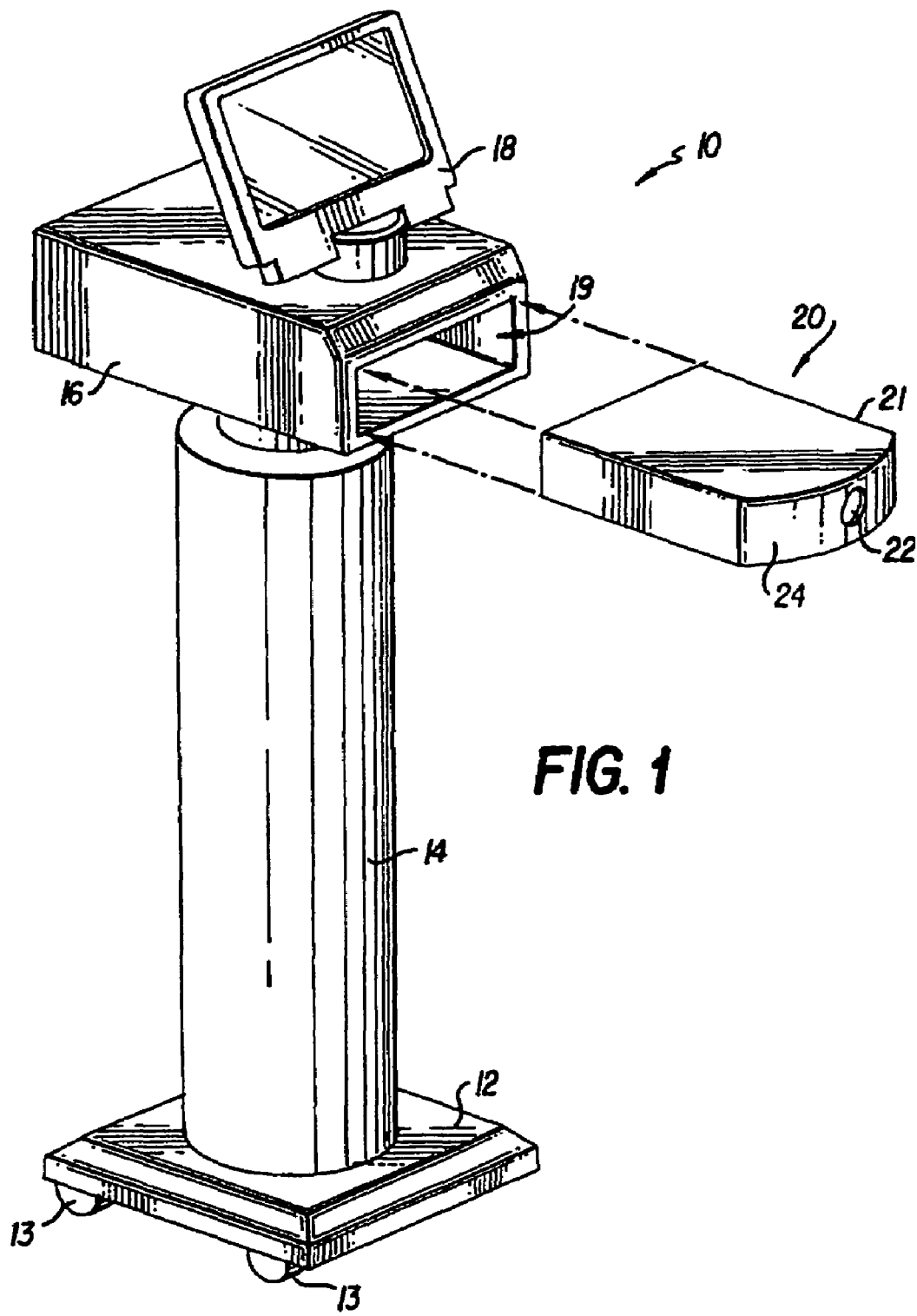
FIG. 1 an example of an afterloading apparatus according to the state of the art.

FIG. 1 illustrates an embodiment of an afterloading apparatus according to the state of the art and is designated generally by reference numeral 10. The afterloading apparatus 10 comprises a base 12, which is preferably placed on wheels 13, a pedestal 14 and a head 16. The head 16 is vertically adjustable with respect to the pedestal 14 by means of an adjustment mechanism (not shown). An appropriate handle (not shown) may be mounted to the base or pedestal 14 for use in positioning the apparatus 10 in a desired location in the vicinity of a patient.

The head 16 may support a video monitor screen 18, such as a LCD touch screen display or the like. The presence and use of such screen for programming and controlling purposes may be optional. Especially afterloading devices equipped with HDR or PDR sources are not provided with a screen mounted on the head, as programming and controlling such afterloading devices is performed in a control room at a different location properly shielded from the treatment room, in order to remote control the afterloading apparatus.

The front or forward end of the head 16 is provided with a receptable opening 19 for removably receiving a replaceable cartridge or cassette 20.

The cartridge 20 comprises a housing 21 with a source wire guidance channel (not visible) having an outlet opening 22a in the front wall 24 thereof. The cartridge 20 contains two elongate wires, namely, an active source wire and a dummy test wire, each stored on a respective storage/drive drum, a radiation shield or safe and necessary sensing, monitoring and software components of the system. Optionally, the cartridge 20 can be provided with suitable drive or transport means for advancing the source wire and/or the test wire through the guidance channel and the outlet opening 22a through a catheter guide tube (not shown) connected to said source wire outlet opening 22a towards a tumour in an animal body.

The medical procedure initiates with placing the afterloading apparatus together with a cartridge 20 inserted into the receptable opening 19 near the patient to be treated. Prior to the radiation treatment one or more guide tubes (catheters, needles, or other closed pathways) are positioned/inserted into the patient's body in or near a cancerous tumour to be treated. Said guide tubes are connected to the source wire opening 22a (or a multiple of source wire openings) and source wire drive means (not shown) present in the cartridge 20 or in the head 16 are activated for advancing the source wire together with the energy emitting source through an internal guidance path within the cartridge 20, through the outlet opening 22a and through the guide tube (not shown) connected to this outlet opening 22a towards or near the tumour to be treated. Subsequently the energy emitting source delivers a therapeutic, predetermined dose of radiation (e.g. under the principle of radioactive decay of radioactive material) to the tumour during specific pre-planned periods of time.

After the radiation treatment the source wire drive means retract the source wire together with the energy emitting source within the cartridge 20. Subsequently the source wire can be advanced through another catheter tube towards a different location near or in the tumour to be treated. Thus dependent on the necessary pre-planned treatment it is possible to perform multiple treatment sessions with the same radioactive source on multiple, different treatment locations within a patient's body.

The energy emitting source at the end of the source wire must be handled with extreme care. Even short exposures at close distances can result in radiation injury. It is therefore extremely important that the afterloading apparatus, which controls the advancement and retraction of the source wire within the catheter tube, operates with a high reliability, and that it is configured to position the source wire within the catheter tube and the animal body in a controllable manner and with extreme accuracy and precision.

In the FIGS. 2-5 several side and upper views are shown of an embodiment of an sensing device according to the invention. The FIGS. 2-5 show the sensing device in several operational stages. For clarity reasons all corresponding parts are indicated with the same reference numerals.

The sensing device 30 (see FIG. 2a-2b) comprises a housing 31, which housing 31 is part of the head 16 of the after loading apparatus or said cartridge 20 as for example shown in FIG. 1. The housing 31 has a guidance channel 32 with an outlet opening 22a, which outlet opening 22a can correspond with the outlet opening 22a of the cartridge of FIG. 1. As described with reference to FIG. 1, in said guidance channel 32 a source wire 33 is accommodated having a distal end 33a, to which end an energy emitting source 34 is fixed. Said energy emitting source 34 can be for example radioactive source, which source has to be positioned at a desired location within an animal body, for example for branchytherapy treatment of prostate cancer.

As already described above a catheter tube (not shown) is connected with the outlet opening 22a extending the guidance path through which the source wire 33 together with the energy emitting source 34 can be advanced or inserted using suitable source wire drive means (not shown) being part of the afterloading apparatus.

As stated above when the afterloading apparatus is not in use knowledge whether the distal end 33a and the energy emitting source 34 are properly retracted until within the safety container of the afterloading apparatus is very important, as the energy emitting source 34 and more in particularly a radioactive source such as a HDR-source (High Doses Rate) has to be handled with extreme care, in order to avoid hazardous and harmful situations like radiation injury.

To this end the afterloading apparatus is provided with a sensing device 30, which is capable of sensing the presence of the distal end 33a and the energy emitting source 34 at several important operational positions within the afterloading apparatus or patient.

The sensing device 30 comprises a lever element 35 which is pivotally mounted within the housing 31. Due to this pivotally construction the lever element 35 can pivot about a pivoting point 36.

Figure 2A:
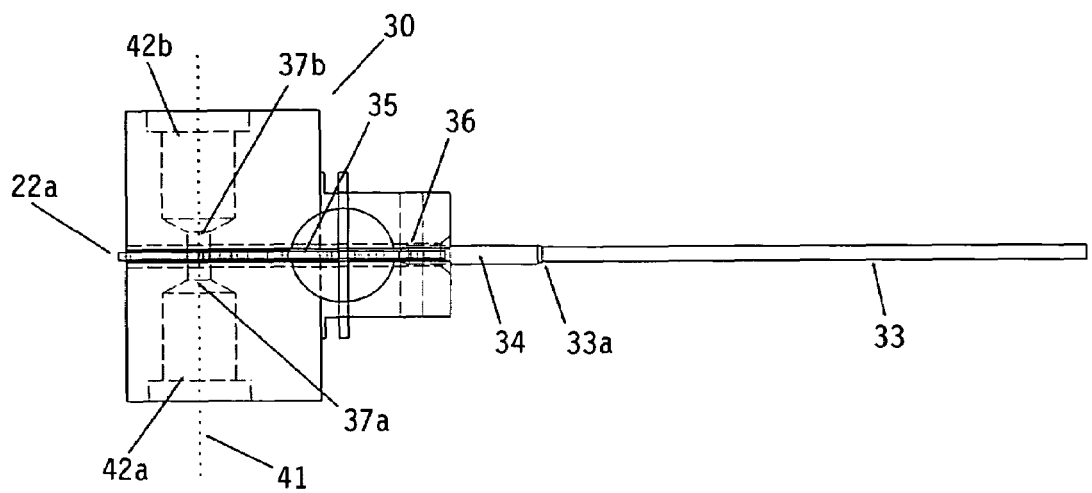
FIGS. 2-5 several side and upper views of an embodiment of a sensing device according to the invention in different operational stages.

In FIG. 2a the lever element 35 is depicted in a first position, indicating that the distal end 33a (and the energy emitting source 34) of the source wire 33 are in a safe storage position within the afterloading apparatus. In this first position a part 35a of the lever element 35 extends in said guidance channel 32 blocking the passageway of the source wire 33 in the direction of the outlet opening 22a.

In this situation (first position) said lever element 35 is biassed against a counterforce, which counterforce urges said lever element 35 in its first position as shown in FIG. 2a. More in particularly said counterforce is exerted on said lever element 35 using a spring 40.

The sensing device according to the invention comprises further more detection means 37a-37b, which in this embodiment detect the presence of said lever element 35 in its first position as shown in FIG. 2a. The presence of the lever element 35 in its first position (FIG. 2) is detected by detection means 37a-37b, which in a specific embodiment use the principle of light path interruption.

Figure 2B:
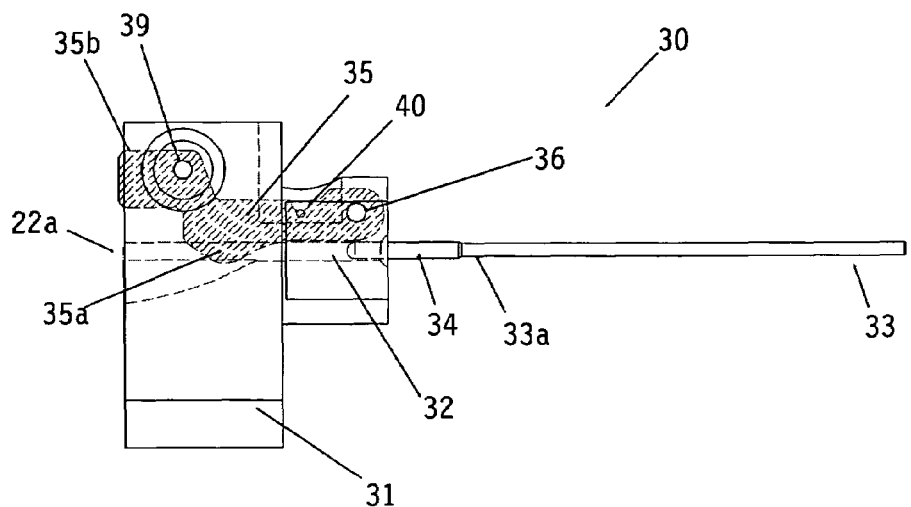
Figure 3:
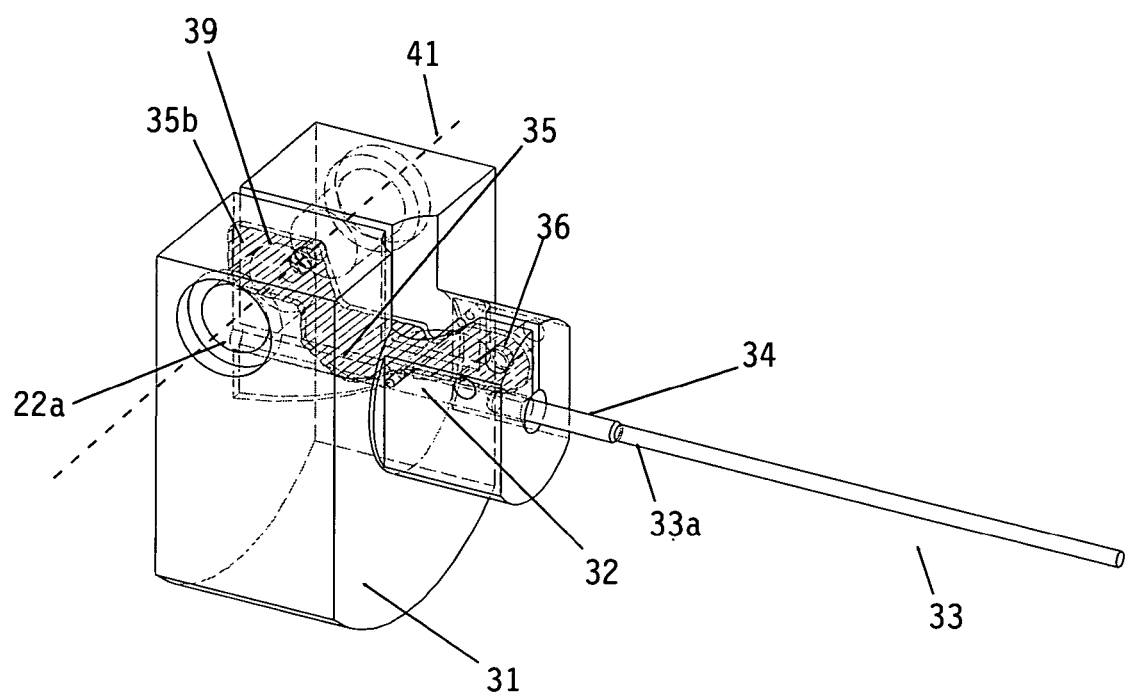

To this end a flange part 35b of said lever element 35 is provided with a through bore 39, which through bore 39 is in alignment with the light path 41 between a light emitting element 37a and a light detector 37b, when said lever element 35 is in its first position of FIG. 2b. Said light emitting element 37a and said detector 37b are mounted on both sides of said flange 35b of said lever element 35.

For a proper functioning of the detection means 37a-37b said flange 35b is made from a light non-transparent material. When the lever element 35 occupies its first position as shown in FIG. 2b, the light path as indicated by the dotted line 41 in the FIGS. 2a-2b is not interrupted by the light non-transparent flange 35b of the lever element 35. Light emitted by said light emitting element 37a can propagate through said opening 39 and can impinge on said light detector 37b, generating an electrical signal indicating that the lever element 35 is present in its first position.

Thus the fact than an electrical signal with a certain magnitude is generated by the light detector 37b clearly and unambiguously indicates that the distal end 33a and the energy emitting source 34 mounted to said distal end are present in the storage position as shown in FIG. 2a-2b.

Unlike the prior art sensing devices this mechanical construction of a lever element gives an accurate and reliable indication about the passage of the energy emitting source passed its reference position within the afterloading apparatus, whereas the lever element is not susceptible for any disturbances, like debris from the catheter tube (not shown) which debris may accumulate within the guidance channel 32 due to the advancement and the retraction of the source wire 33 within the guide tube. The reliability and accuracy of the sensing device is ensured, as the detection means 37a-37b are mounted in a separate cavity or place 42a-42b within the housing 31, which cavity 42a-42b are isolated from the guidance channel 32.

Thus any debris from the inner side of the catheter tube (not shown) accumulated within the guidance channel 32 can not affect the effectiveness and accuracy of the detection means 37a-37b. With this construction a more accurate and reliable sensing device is obtained compared with the prior art as the debris can not accumulate at the side of the detection means (light detector 37b). The view of the optical light detector 37b is not obscured by this debris.

Furthermore, as the light path formed by the detection means 37a-37b does not coincide with the passageway of the energy emitting source 34 through the guidance channel 32, especially the light detector 37b will not be irradiated by the energy emitting source 34, expanding its life span.

Moreover unlike the prior art embodiments the sensing device according to the invention does not measures and/or detects the presence of the energy emitting source within the guidance channel using the source wire itself. Therefore the dimensions of the energy emitting source and/or the source wire do not affect the accuracy of the measurements and this allows the use of source wires having a significant smaller diameter.

When the source wire drive means (not shown) of the afterloading apparatus are activated for advancing the source wire 33 together with the energy emitting source 34 mounted to the distal end 33a in the direction towards the outlet opening 22a, said energy emitting source 34 is urged against the part 35a of said lever element 35, which part 35a extends in said guidance channel 32. This situation wherein the energy emitting source 34 is urged against said part 35a of the lever element 35 shown in FIG. 4a-4b.

Figure 4A:
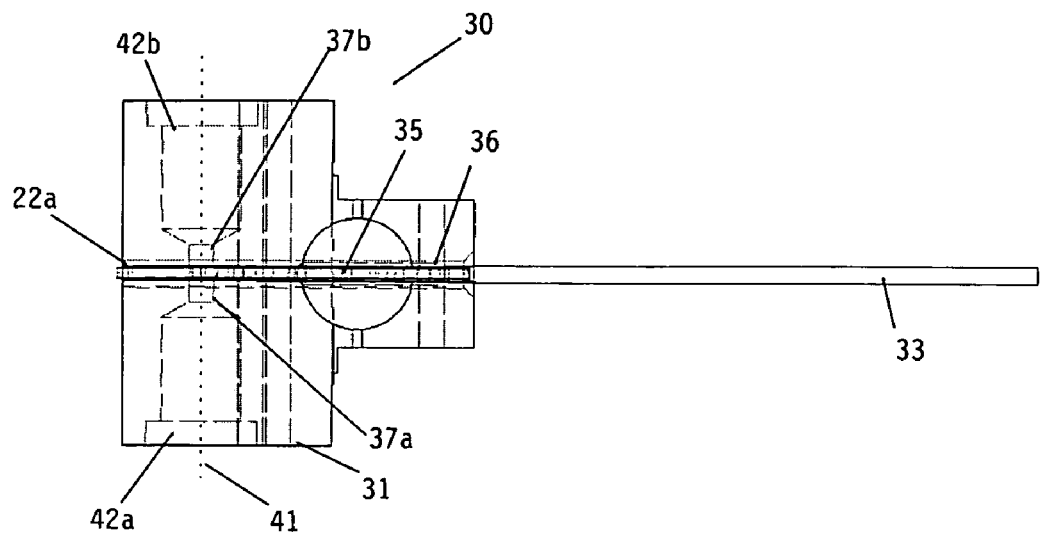
Figure 4B:
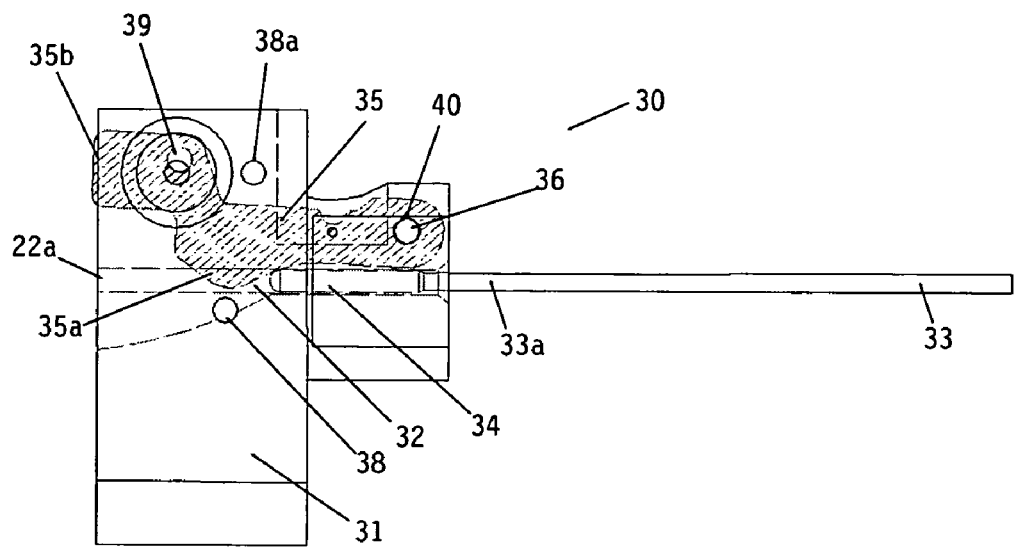

This advancement of the source wire 33 against said part 35a results in a pivotal movement of said lever element 35 around its pivotal point 36 towards a second position. Due to this pivotal movement the opening 39 becomes less and less in alignment with the light emitting element 37a and said light detector 37b. The optical path 41 between the light emitting element 37a and the light detector 37b is partly interrupted by the light non-transparent flange 35a of the lever element 35, as shown in FIG. 4b. This interruption of the light path way causes a change in the electronic signal received by said light detector 37b. Said change is detected and processed by suitable control means and serves as an indication for the pivotal displacement of the lever element 35 towards its second position and the location of the source 34 at its reference position within the guidance channel 32 as shown in FIG. 4b.

This reference position of the energy emitting source 34 within the guidance channel serves as a starting point for the wire drive means for subsequent advancement of the source wire through the guidance channel 32, the catheter tube towards the treatment position in the patient, enabling an accurate determination of the exact position of the energy emitting source 34 within the catheter tube/patient.

Figure 5A:
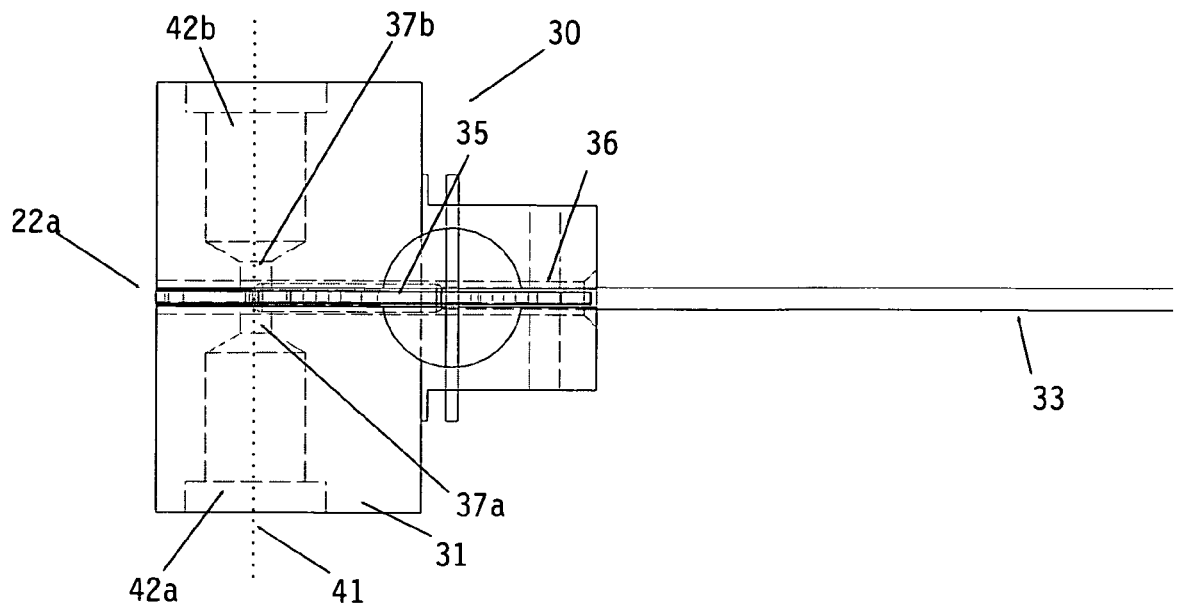
Figure 5B:
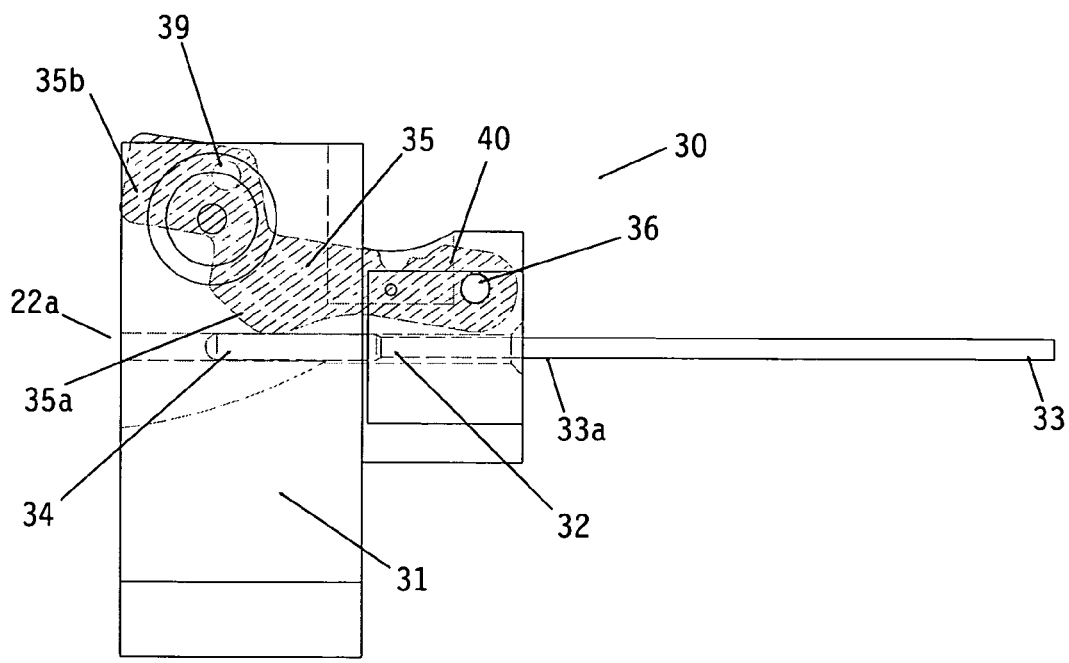

Subsequent advancement of the source wire 33 further displaces said part 35a resulting in a pivotal movement of said lever element 35 around its pivotal point 36 towards a third position, as depicted in FIG. 5a-5b. Due to this pivotal movement the opening 39 brought further out of alignment with the light emitting element 37a and said light detector 37b. The optical path 41 between the light emitting element 37a and the light detector 37b is fully interrupted by the light non-transparent flange 35a of the lever element 35. The absence of any light impinging on the light detector 37b as emitted by the light emitting element 37a, gives an electronic signal (or the absence of any electronic signal) clearly indicating that the energy emitting source 34 has passed its reference point of FIG. 4b.

The presence of the lever element 35 in its third position (FIG. 5b) clearly indicates, that the distal end 33a and the energy emitting source 34 are advanced through said guidance channel 32 passed said lever element 35 towards the outlet opening 22a indicating that the energy emitting source 34 is no longer present in its reference position. This means that the energy emitting source 34 is present within the catheter tube (not shown) towards desired location within the animal body unambiguously indicating that the afterloading apparatus should be handled/treated with upmost care in order to avoid harmful en hazardous situations.

With the knowledge of the exact reference position of the energy emitting source 34 it is now possible to accurately position the source 34 at any desired location within the catheter tube/patient for treatment purposes using the source wire drive means and proper positioning means, like a stepper motor or encoding means. This allows to perform treatment sessions more accurately without the hazard of positioning the energy emitting source at a wrong treatment location within the patient.

The lever element 35 has now reached its third position as shown in FIG. 5a-5b and is kept in said position by said source wire 33. Said lever element 35 is still subjected to a counterforce exerted by said spring 40 urging said lever element 35, now being present in its third position, towards its first position.

Although the embodiment of the sensing device according to the invention has been described with detection means based on principle of interruption of an optical path, also other parts of detection means are possible.

In another embodiment the detection means operate according the electromagnetic principle, wherein the flange 35a of the lever element is partly made of an magnetic material and whereas the detection means comprise one or more Hall sensors placed at both sides of the flange 35a within the cavity 42a-42b. Said Hall sensors are e.g. manufactured as a coil. The displacement of the lever element 35 from its first position towards its second position and third position about the pivotal point 36 due to the advancement of the source wire 33 with its distal end 33a and the energy emitting source 34 results in the displacement of the magnetic part of said flange 35a passing the Hall sensors 37a-37b, creating or inducing an changing induction current signal according to the Hall principle.

This induction current signal is used for indicating whether the lever element 35 is in its second position (or third position) indicating that the energy emitting source 34 is in its reference position (or has passed its reference position).

In another embodiment the detection means may comprise one or more switches, for example microswitches, which switches are activated and/or deactivated when said lever element 35 arrives in its first, second and/or third position.

Also said flange 35a may be provided with two openings 39 and said detection means 37a-37b may include two optical sets of light emitting elements 37a and light detectors 37b. Each optical set uses one of said openings 39 as light path. This embodiment incorporates a fail safe situation in the event that one of the optical sets malfunctions. During proper operation both light paths through the two openings will be interrupted simultaneously, due to the pivotal displacement of the lever element 35 around its pivoting point 36 from its first position towards its second position and third position. Thus two identical electronic signals will be generated. The absence of one of these two signals clearly indicates the malfunction of the corresponding optical set.

Likewise when the source wire 33 is retracted back into the afterloading apparatus the displacement of the distal end 33a and the energy emitting source 34 through the guidance channel 32 passed the lever element 35 results in a returning displacement of the lever element 35 from its third position (FIG. 5) towards its initial first position (FIG. 2) due to the counterforce exerted on said lever element 35 by said spring 40.

At the time the lever element 35 reaches its second position as shown in FIG. 4, the detection means will generate a corresponding signal as the light path through the opening 39 becomes no longer fully interrupted and said opening starts to become in full alignment with the lightpath 41 between the light emitting element 37a and the light detector 37b.

This situation wherein light emitted by the light emitting element 37a can now impinge on the light detector 37b will cause the generation of (a change in) an electronic signal. The magnitude or amount of this signal will unambiguously indicate that the lever element 35 has reached its second position.

The exact length of the source wire 33 (with energy emitting source 34) as inserted from its reference position towards a desired position within the catheter tube in the patient's body is known as the source wire drive means are provided with accurate positioning means, like a stepper motor or other suitable encoding means. Therefore the retraction of the source wire back into the afterloading apparatus over the same length as inserted must coincide with the pivotal movement of the lever element 35 from its third position (FIG. 5) towards its second position (FIG. 4).

In the unexpected and unwanted event that the source wire 33 breaks inside the catheter tube the energy emitting source 34 will remain inside the catheter tube and the patient's body creating an hazardous situation for both the patient and his environment. This situation can be noticed quickly with the sensing device according to the present invention as the broken source wire has now a shorter length and will cause the lever element 35 to pivot earlier from its third position towards its second position as in the normal situation.

The source wire drive means will notice that in such event the source wire is retracted over a shorter length than required and they will generate an appropriate notification (alarm sound or message) for the medical personel in order to take appropriate steps.

It will be clear that with a sensing device according to one or more embodiments of the invention a reliable and accurate detection of the presence of the distal end and more in particularly of the energy emitting source mounted to the distal end at its save storage/reference position within the afterloading apparatus is obtained and that hazardous and harmful situations, such as accidentally radiation exposure are avoided.

In the drawings the sensing device according to the invention has been described with detection means operating according the principle of interruption of an optical path, which detection means cooperate with at least one through bore present in the lever element 35. It will be clear for the skilled man that the principle as described also properly functions without the use of a through bore, as the optical path between the light emitting element and the light detector can also be interrupted by an (upper, lower or side) edge of the lever element during its pivotal displacement within the housing.

Furthermore the edge of the lever element can be provided with one or more notches, which notches each coincide with their corresponding optical light path.

The invention claimed is:

1. A device for sensing the presence of the distal end of a source wire in a reference position within a guidance channel of an afterloading apparatus, said afterloading apparatus being used for positioning an energy emitting source fixed to said distal end of said source wire at a desired position within an animal body for radiation therapy treatment purposes, by driving said source wire from said reference position towards said desired position through said guidance channel and a catheter tube, which catheter tube is connected with one tube end to the afterloading apparatus and implanted with its other tube end in said animal body, the sensing device comprising a lever element pivotally mounted near said guidance channel, which lever element is urged by said distal end in a first position, when said distal end of said source wire is not present in its reference position and whereas said lever element is in a second position, when said distal end is present in its reference position, and
  wherein said lever element is urged by said distal end in a third position when said distal end is past said reference position and wherein detecting means are present for detecting the presence of said lever element in said first, second or third position.

2. The sensing device according to claim 1, wherein said first position said lever element extends in said guidance channel.

3. The sensing device according to claim 1, wherein said lever element is biased against a counterforce, said counterforce urging said lever element in its first position.

4. The sensing device according to claim 3, wherein said device further comprises a spring for exerting said counterforce on said lever element.

5. The sensing device according to claim 1, further comprising detection means for detecting the presence of said lever element in said first, second or third position.

6. The sensing device according to claim 5, wherein said detection means comprises at least one light emitting element and one light detector mounted at both sides of said lever element.

7. The sensing device according to claim 6, wherein said lever element is at least partly made of a light non-transparent material.

8. The sensing device according to claims 6, wherein said lever element is provided with at least one through bore.

9. The sensing device according to claims 6, wherein an edge of said lever element is provided with at least one notch.

10. The sensing device according to claim 5, wherein the optical path formed by said light emitting element and said light detector is located some distance away from the guidance channel.

11. The sensing device according to claim 5, wherein said lever element is made of a magnetic material and wherein said detection means comprises a Hall-sensor.

12. The sensing device according to claim 5, wherein detection means comprises at least one switch, preferably a microswitch.

13. The sensing device according to claim 1, wherein the energy emitting source is radio-wave antenna.

14. The sensing device according to claim 1, wherein the energy emitting source is miniature X-ray source.

15. The sensing device according to claim 1, wherein the energy emitting source is a radioactive source.

16. The sensing device according to claim 1, wherein the source wire is an optical wire.

17. The sensing device according to claim 1, wherein the source wire is a coaxial cable.

18. The sensing device according to claim 1, wherein the source wire is a nickel-titanium alloy wire.

19. The sensing device according to claim 1, wherein the source wire is a combination of optical wire surrounded by a nickel-titanium alloy tube.

20. The sensing device according to claim 1, wherein the source wire is a combination of a coax cable and an optical wire.

21. An afterloading apparatus provided with a sensing device according to claim 1.

* * * * *